United States Patent
Hong et al.

(10) Patent No.: US 10,350,294 B2
(45) Date of Patent: Jul. 16, 2019

(54) PHARMACEUTICAL COMPOSITIONS TO REDUCE COMPLICATIONS OF OCULAR STEROID

(71) Applicants: TAIWAN LIPOSOME COMPANY, LTD., Taipei (TW); TLC BIOPHARMACEUTICALS, INC.

(72) Inventors: Keelung Hong, South San Francisco, CA (US); Luke S. S. Guo, South San Francisco, CA (US); Sheue-Fang Shih, Taipei (TW); Po-Chun Chang, Taipei (TW); Chih-Chiang Tsai, Taipei (TW); Hong-Hul Lin, Taipei (TW); Yun-Long Tseng, Taipei (TW)

(73) Assignees: TAIWAN LIPOSOME COMPANY, LTD., Taipei (TW); TLC BIOPHARMACEUTICALS, INC., South San Francisco, CA (US)

( * ) Notice: Subject to any disclaimer, the term of this patent is extended or adjusted under 35 U.S.C. 154(b) by 0 days.

(21) Appl. No.: 15/913,466

(22) Filed: Mar. 6, 2018

(65) Prior Publication Data

US 2018/0193461 A1 Jul. 12, 2018

Related U.S. Application Data

(62) Division of application No. 14/377,211, filed as application No. PCT/US2013/025390 on Feb. 8, 2013, now Pat. No. 10,058,616.

(60) Provisional application No. 61/597,189, filed on Feb. 10, 2012.

(51) Int. Cl.
| | |
|---|---|
| A61K 31/573 | (2006.01) |
| A61K 31/575 | (2006.01) |
| A61K 31/661 | (2006.01) |
| A61K 31/683 | (2006.01) |
| A61K 47/24 | (2006.01) |
| A61K 9/00 | (2006.01) |
| A61K 9/127 | (2006.01) |
| A61K 47/10 | (2017.01) |
| A61K 47/28 | (2006.01) |
| A61K 47/02 | (2006.01) |

(52) U.S. Cl.
CPC ............ *A61K 47/24* (2013.01); *A61K 9/0048* (2013.01); *A61K 9/127* (2013.01); *A61K 31/573* (2013.01); *A61K 31/575* (2013.01); *A61K 31/661* (2013.01); *A61K 31/683* (2013.01); *A61K 47/02* (2013.01); *A61K 47/10* (2013.01); *A61K 47/28* (2013.01)

(58) Field of Classification Search
CPC .. A61K 31/573; A61K 31/575; A61K 31/661; A61K 31/683
See application file for complete search history.

(56) References Cited

U.S. PATENT DOCUMENTS

| | | | |
|---|---|---|---|
| 4,804,539 A | 2/1989 | Guo et al. | |
| 2011/0033468 A1* | 2/2011 | Shih | A61K 9/0019 424/139.1 |
| 2013/0217657 A1* | 8/2013 | Lindstrom | A61K 31/722 514/171 |

* cited by examiner

*Primary Examiner* — Zohreh A Fay
(74) *Attorney, Agent, or Firm* — Leason Ellis LLP

(57) ABSTRACT

The present invention relates to pharmaceutical compositions comprising a combination of a lipid cake mixture comprising one or more phospholipids, with or without cholesterol, and a steroid solution comprising an ocular steroid, derivative thereof, a pharmaceutically acceptable salt thereof or a prodrug thereof, wherein the total amount of the phospholipid in the said composition is about 0.1 umol to less than about 2.5 umol per 50 ul of pharmaceutical composition and the side effects of the ocular steroid are reduced. The pharmaceutical composition is preferably administered by ocular route to treat ophthalmic diseases.

9 Claims, No Drawings

PHARMACEUTICAL COMPOSITIONS TO REDUCE COMPLICATIONS OF OCULAR STEROID

TECHNOLOGY FIELD

The present invention relates to pharmaceutical compositions comprising a combination of lipid cake and a steroid solution to reduce the side effects of steroid and methods of their use in treating ophthalmic diseases.

BACKGROUND OF THE INVENTION

Macular edema produces loss of central vision and is a clinical manifestation of diabetic retinopathy. It is due to retinal microvascular changes, and the pathogenesis is not only related to VEGF dependency but also to other inflammatory and angiogenic cytokine levels that can be suppressed by corticosteroids. (Sohn H J et al. Changes in aqueous concentrations of various cytokines after intravitreal triamcinolone versus bevacizumab for diabetic macular edema. Am J Ophthamol. October 2011; 152(4):686-94.)

Intravitreal corticosteroid injection can be a treatment option for some cases of chronic macular edema not reacting to classic treatment such as laser photocoagulation, periocular and systemic steroids or carbonic anhydrase inhibitors.

Intravitreal corticosteroid injection is also used to treat uveitis and to improve the visual acuity in patients with branch retinal vein occlusion or central retina vein occlusion. However, repetitive intravitreal injection is required to maintain the optimal and efficient corticosteroid concentration in the eye, and this is associated with complications such as infectious endophthalmits, retinal detachment, traumatic cataract and increase intra-ocular pressure (IOP). One study shows the incidence of increased IOP after intravitreal steroid injection was 57.69% at one month, and 75 and 47.05%, at 3 and 6 months, respectively and progression of cataract was found in 22.72% of the patients. (Oarcla Fernández M et al. Intravitreal triamcinolone acetonide use in diffuse persistent diabetic macular edema. Arch Soc Esp Oftalmol 2011 October; 86(10):314-319.)

In view of the deficiencies outlined above, there is a need for intravitreal steroid injection with reduced side effects.

BRIEF SUMMARY OF THE INVENTION

The present invention is directed to a pharmaceutical composition comprising a combination of a lipid cake mixture comprising a phospholipid or mixture of phospholipids, with or without cholesterol; and a steroid solution comprising an ocular steroid, a derivative thereof, a pharmaceutically acceptable salt thereof or a prodrug thereof wherein the total amount of phospholipids is less than about 2.5 umol per 50 ul of said pharmaceutical composition and reduces the side effects of said ocular steroid, said derivative, said pharmaceutically acceptable salt or said prodrug relative to a composition having at least about 5 umol of phospholipids per 50 ul of pharmaceutical composition.

The pharmaceutical composition can be prepared by mixing the lipid cake with a steroid solution, wherein the steroid solution comprises an ocular steroid, a derivative thereof, a pharmaceutically acceptable salt thereof, or a prodrug thereof.

The present invention is also directed to methods of treating ophthalmic diseases in a subject in need thereof. The methods comprise the steps of: administering to the subject a pharmaceutical composition described herein, whereby the symptoms in the subject are reduced. The present invention is particularly useful for treating ophthalmic diseases confined to the posterior segment of the eye by ocular delivery.

DETAILED DESCRIPTION OF THE INVENTION

Definition

As employed above and throughout the disclosure, the following terms, unless otherwise indicated, shall be understood to have the following meanings.

As used herein, the singular forms "a," "an," and "the" include the plural reference unless the context clearly indicates otherwise.

As used herein, the term "about," when referring to a measurable value such as an amount, a temporal duration, and the like, is meant to encompass variations of ±10%, preferably ±5%, more preferably ±1%, and even more preferably ±0.1% from the specified value, as such variations are appropriate to reduce the side effect of steroid, unless other specified. As used herein, the term "about," when referring to a range, is meant to encompass variations of ±10% within the difference of the range, preferably ±5%, more preferably ±1%, and even more preferably ±0.1% from the specified value, as such variations are appropriate to reduce the side effect of steroid, unless other specified.

The term "liposome" as used herein means vesicles comprised of concentrically ordered lipid bilayers encapsulating an aqueous phase, or small or large unilamellar vesicles.

An "effective amount," as used herein, refers to a dose of the pharmaceutical composition that is sufficient to reduce the symptoms and signs of ophthalmic disease, such as blurry, washed out vision.

The term "treating," "treated," or "treatment" as used herein includes preventative (e.g. prophylactic), palliative, and curative uses or results.

The term "subject" includes a vertebrate having ophthalmic diseases. Preferably, the subject is a warm-blooded animal, including mammals, preferably humans.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity.

"Pharmaceutically acceptable salts" of the ocular steroid of the present invention are salts of an acidic steroid formed with bases, namely base addition salts such as alkali and alkaline earth metal salts, such as sodium, lithium, potassium, calcium, magnesium, as well as 4 ammonium salts, such as ammonium, trimethyl-ammonium, diethylammonium, and tris-(hydroxymethyl)ethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided to a basic ocular steroid.

In one aspect, the present invention provides a pharmaceutical composition comprising a combination of a lipid cake mixture comprising a phospholipid or mixture of phospholipids, with or without cholesterol; and a steroid solution comprising an ocular steroid, a derivative thereof, a pharmaceutically acceptable salt thereof or a prodrug thereof in double-distilled water (ddH$_2$O) or a suitable buffer, wherein the total amount of phospholipids in said composition is less than about 2.5 umol per 50 ul of pharmaceutical composition and reduces the side effects of said steroid, said derivative, said pharmaceutically acceptable salt or said prodrug relative to a composition having at least about 5 umol of phospholipids per 50 ul of pharmaceutical composition. Another aspect of the present invention is directed to methods of treating ophthalmic diseases, comprises the administration of an effective amount of the pharmaceutical composition describe herein to a subject in need thereof, whereby the symptoms and signs of the ophthalmic diseases in the subject are reduced.

Lipid Cake

The lipid cake in the present invention refers to a solid lipid mixture in a cake, film or powder.

In one embodiment, the phospholipid or mixture of phospholipids, with or without cholesterol, are pre-formed into liposomes before further processing into a lipid cake.

In another embodiment, the phospholipid or mixture of phospholipids, with or without cholesterol, are not pre-formed into liposomes before further processing into a lipid cake The liposomes are nano-sized and comprise a particle-forming component and an agent-carrying component. The particle-forming component forms an enclosed lipid barrier.

The lipid cake can be prepared from a variety of lipids capable of either forming or being incorporated into a unilayer or bilayer structure. The lipids used in the present invention include one or more phospholipids, with or without cholesterol. Examples of the phospholipid used in the present invention include, but are not limited to, phosphatidylcholine (PC), phosphatidylglycerol (PG), phosphatidylethanolamine (PE), phosphatidylserine (PS), phosphatidic acid (PA), phosphatidylinositol (PI), egg phosphatidylcholine (EPC), egg phosphatidylglycerol (EPG), egg phosphatiiylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI), dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), dioleoylphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleoylphosphatidylethanolamine (DOPE), palmitoylisearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC) polyethyleneglycol distearoylphosphatidylethanolamine (PEO-DSPE), dipalmitoylpbosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoyl-phosphatidylinositol (DPPI), 1,2-dioleoyl-an-glycero-3-phosphatidylinositol (DOPI), dimyristoylphosphatidylinositol (DMPI), distearoylphosphatidylinositol (DSPI), and a mixture thereof. Particularly preferred phospholipids are selected from the group consisting of DOPC and DOPG In one embodiment, the lipid cake mixture comprises of DOPC, DOPG and cholesterol at a molar ratio of 29.5% to 90%:3% to 37.5%:10% to 33%. In another embodiment, the lipid cake mixture comprises of about 15% to less than about 30% molar ratio of cholesterol. In another embodiment, the lipid cake mixture comprises about 18 to about 28% molar ratio of cholesterol. In yet another embodiment, the lipid cake mixture comprises about 20 to about 25% molar ratio of cholesterol.

In one embodiment, the particle-forming component is free of fatty acid or cationic lipid (i.e. a lipid carrying a net positive charge a physiological pH).

In another embodiment, the particle-forming component includes a hydrophilic polymer with a long chain of highly hydrated flexible neutral polymer attached to a phospholipid molecule. Without being bound by any theory, the hydrophilic polymer is believed to stabilize the liposome and result in a longer circulation time in vivo. Examples of the hydrophilic polymer include, but are not limited to, polyethylene glycol (PEG) with a molecular weight about 2,000 to about 5,000 daltons, methoxy PEG (mPEG), ganglioside $GM_1$, polysialic acid, polylactic (also termed polylactide), polyglycolic acid (also termed polyglycolide), apolylacticpolyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose and synthetic polymers.

The particle-forming component may further comprise a lipid-conjugate of an antibody or a peptide that acts as a targeting moiety to enable the liposome to specifically bind to a target cell bearing a target molecule. Examples of the target molecules include, but are not limited to, epidermal growth factor receptor (EGFR), vascular endothelial growth factor receptor (VEGF), carcinoembryonic antigen (CEA), and erbB-2/neu (HER2).

The liposomes prepared in this invention can be generated by conventional techniques used to prepare vesicles. These techniques include the ether injection method (Deamer et al., Acad. Sci. (1978) 308: 250), the surfactant method (Brunner t al., Biochim. Biophys. Acts (1976) 455: 322), the freeze-thaw method (Pick et al., Arch. Biochim. Biophys. (1981) 212: 186), the reverse-phase evaporation method (Szoka et al., Biochim. Biophys. Acts. (1980) 601: 559 71), the ultrasonic treatment method (Huang et al., Biochemistry (1969) 8: 344), the ethanol injection method (Kremer et al., Biochemistry (1977) 16: 3932), the extrusion method (Hope at al., Biochim. Biophys. Acta (1985) 812:55 65), the French press method (Barenholz et al., FEBS Lett. (1979) 99: 210) and methods detailed in Szoka, F., Jr., et al., Ann. Rev. Biophys. Bioeng. 9:467 (1980). All of the above processes are basic technologies for the formation of liposome vesicles and these processes are incorporated by reference herein. After sterilization, the pre-formed liposomes are placed aseptically into a container and then lyophilized to form a powder or a cake. Because the lipid cake mixture comprising pre-formed liposomes in the present invention are lyophilized, at least one cryoprotectant is required for the preparation of the lipid cake. In one embodiment, the lipid cake mixture further comprises one or more buffers.

The cryoprotectants include, but are not limited to, mannitol, glycerol, dextrose, sucrose, and/or trehalose. One preferred cryoprotectant is mannitol.

The buffers include, but are not limited to, sodium phosphate monobasic dihydrate and sodium phosphate dibasic anhydrous.

In the embodiment where the lipid cake comprises lipids that are not pre-formed into liposomes, the lipid cake can be prepared by dissolving in a suitable organic solvent, including, but not limited to, ethanol, methanol, t-butyl alcohol, ether and chloroform, and can be dried by heating, vacuum evaporation, nitrogen evaporation, lyophilization, or other conventional means of solvent removal.

Specific examples of lipid cake preparation in support of the present invention will be described below.

Steroid Solution

The steroid solution in the present invention comprises of an ocular steroid, a derivative thereof a pharmaceutically acceptable salt thereof, or a prodrug thereof.

The ocular steroid useful in the present invention includes any naturally occurring steroid hormones, synthetic steroids and their derivatives. Examples of the ocular steroid include, but are not limited to, cortisone, hydrocortisone, hydrocortisone acetate, tixocortol pivalate, fluocinolone, prednisolone, methylprednisolone, prednisone, triamcinolone acetonide, triamcinolone, mometasone, amcinonide, budesonide, desonide, fluocinonide, fluocinolone acetonide, halcinonide, betamethasone, betamethasone sodium phosphate, dexamethasone, dexamethasone sodium phosphate (DSP), fluocortolone, hydrocortisone-17-butyrate, hydrocortisone-7-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, difluprednate, loteprednol, fluorometholone, medrysone rimexolone, beclomethasone, cloprednol, cortivazol, deoxycortone, difluorocortolone, fluclorolone, fluorocortisone, flumethasone, flunisolide, fluorocortolone, flurandrenolone, meprednisone, methylprednisolone and paramethasone. In a preferred embodiment, the ocular steroid is a water soluble steroid. In a more preferred embodiment, the ocular steroid is DSP.

The pharmaceutically acceptable salts of the ocular steroid include non-toxic salts formed from non-toxic inorganic or organic bases. For example, non-toxic salts can be formed with inorganic bases such as an alkali or alkaline earth metal hydroxide, e.g., potassium, sodium, lithium, calcium, or magnesium; and with organic bases such as an amine and the like.

The pharmaceutically acceptable salts of the ocular steroid also include non-toxic salts formed from non-toxic inorganic or organic acids. Example of organic and inorganic acids are, for example, hydrochloric, sulfuric, phosphoric, acetic, succinic, citric, lactic, maleic, fumaric, palmitic, cholic, pamoic, mucic, D-glutamic, glutaric, glycolic, phthalic, tartaric, lauric, stearic, salicylic, sorbic, benzoic acids and the like.

The steroid solution of the preset invention can be prepared either in ddH$_2$O or a suitable buffer.

The Pharmaceutical Composition

The pharmaceutical composition of the present invention is suitable for ocular delivery of a steroid and comprises a combination of a lipid cake mixture comprising a phospholipid or mixture of phospholipids, with or without cholesterol; and a steroid solution comprising an ocular steroid or a pharmaceutically acceptable salt thereof, wherein the total amount of phospholipids is about 0.1 umol to about less than about 2.5 umol per 50 ul of pharmaceutical composition and wherein the side effects of said composition is reduced relative to the side effects of a pharmaceutical composition having at least about 5 umol of phospholipids per 50 ul of pharmaceutical composition.

In one embodiment, the total amount of phospholipids is about 0.5 umol to less than about 2.0 umol per 50 ul of pharmaceutical composition. In another embodiment, the total amount of phospholipids is about 1 umol to less than about 1.5 umol per 50 ul of pharmaceutical composition In one embodiment, the pharmaceutical composition further comprising at least one pharmaceutically acceptable excipient, diluent, vehicle, carrier, medium for the active ingredient, a preservative, cryoprotectant or a combination thereof.

In one embodiment, the pharmaceutical composition of the present invention is prepared by mixing one or more phospholipids, with or without cholesterol, and one or more buffers to form liposomes, lyophilizing the liposomes with one or more cryoprotectants to form a lipid cake in a powder form. The powdered lipid cake is reconstituted with the steroid solution to form an aqueous suspension.

In another embodiment, the pharmaceutical composition of the present invention is prepared by mixing one or more phospholipids, with or without cholesterol, in a solvent then removing the solvent to form a lipid cake. The lipid cake is reconstituted with the steroid solution to form an aqueous suspension In a preferred embodiment, the pharmaceutical composition comprises about 0.6 to about 0.7 mg of dexamethasone. In another preferred embodiment, the pharmaceutical composition comprises about 0.19 to about 0.59 mg of fluocinolone acetonide. In yet another preferred embodiment, the pharmaceutical composition comprises about 4 mg of triamcinolone acetonide.

The pharmaceutical composition of the present invention comprises about 10% to about 50% of lipid-associated DSP or about 50% to about 90% of non-associated DSP. Non-associated DSP is easily cleared in the vitreous humor with a half-life of about 3.5 hours while the lipid-associated DSP is not readily cleared in the vitreous humor and can be retained in vitreous humor for several months depending on the pharmaceutical compositions.

The pharmaceutical compositions of the invention may be used to treat a patient suffering from ophthalmic diseases. In a preferred embodiment, the ophthalmic disease is confined to the posterior segment of the eye. In a more preferred embodiment, the ophthalmic disease is any one of the following: macular edema, uveitis, branch retinal vein occlusion or central retina vein occlusion, and age-related macular degeneration.

The Method of Treating Ophthalmic Diseases

Another aspect of this invention is a method of treating ophthalmic diseases in a subject, which comprises the administration an effective amount of the pharmaceutical composition as described herein to a subject in need thereof, whereby the symptoms and signs of the ophthalmic diseases in the subject are reduced.

The pharmaceutical composition may be constituted into any form suitable for the mode of administration selected. In one embodiment, the pharmaceutical composition is formulated for ocular administration. In another embodiment, the pharmaceutical composition is formulated for intravitreal administration. In another embodiment, the pharmaceutical composition is formulated for topical administration.

The dosage of the pharmaceutical composition of the present invention can be determined by the skilled person in the art according to the embodiments. Unit doses or multiple dose forms are contemplated, each offering advantages in certain clinical settings. According to the present invention, the actual amount of the pharmaceutical composition to be administered can vary in accordance with the age, weight, condition of the subject to be treated, and depends on the discretion of medical professionals.

The following examples further illustrate the present invention. These examples are intended merely to be illustrative of the present invention and are not to be construed as being limiting Example 1: Preparation of the Lipid Cake The lipid cake was prepared by the ethanol injection method. The lipids, including DOPC, DOPG (both are commercially available from NOF Corporation, Japan and Lipoid LLC, USA) and cholesterol (commercially available from MINAKEM, France), were combined at a molar ratio of 67.5:7.5:25 and dissolved in 99.9% ethanol at about 40° C. in a flask. A tabletop ultrasonic bath was used for lipid dissolution.

The dissolved lipid solution was added to sodium phosphate solution at 100 mL/min by a peristaltic pump and the two solutions were mixed. The lipid mixture was then passed 6-10 times through a polycarbonate membrane with a pore size of 0.2 um. Liposomes (or large unilamellar vesicles) were formed and the average vesicle diameter was about 120-140 nm (measured by Malvern ZetaSizer Nano ZS-90).

The liposome mixture was dialyzed and concentrated by a tangential flow filtration system with Millipore Pellicon 2 Mini Ultrafiltration Module Biomax-100C (0.1 m$^2$), and mannitol was added to obtain a final mannitol concentration of 20 mg/mL. The liposome mixture was then sterilized using a 0.2 um sterile filter and the sterilized liposome mixture was filled aseptically into vials and then lyophilized to form lipid cake. The main compositions of the lipid cake is summarized in Table 1.

TABLE 1

Composition of the Lipid Cake
Composition (Molar Ration)

| DOPC | DOPG | Cholesterol | Sodium Phosphate |
|------|------|-------------|------------------|
| (67.5) | (7.5) | (25) | Solution |

Example 2: Preparation of the Pharmaceutical Composition

The pharmaceutical composition was prepared by reconstituting the lyophilized lipid cake in Example 1 with a DSP solution to form multilamellar vesicles.

For 50 ul of pharmaceutical composition with 0.6 mg of DSP and 5 umol phospholipids, one vial of lyophilized lipid cake in Example 1 was reconstituted with a 0.3 ml of DSP solution wherein the concentration of DSP is 13.2 mg/ml.

For 50 ul of pharmaceutical composition with 0.6 mg of DSP and 2.5 umol phospholipids, one vial of lyophilized lipid cake in Example 1 was reconstituted with a 0.6 ml of DSP solution wherein the concentration of DSP is 13.2 mg/ml.

Example 3. In Vivo Evaluation of the Pharmaceutical Composition in Reducing the Ocular Side Effects of Steroid An in vive evaluation of the effect of the pharmaceutical composition in reducing the side effects of ocular steroid was performed using New Zealand albino rabbit population. 25 Male rabbits, aged between 10.12 weeks, were recruited in the study. The average body weight of the rabbit was 2.3 kg at baseline.

Rabbits had free access to drinking water and food at all time during this trial.

The study design involved 5 study groups as follows:

Group 1: 5 rabbits each received 50 ul of the pharmaceutical composition comprising pre-formed liposomes and 0.05 mg of DSP, wherein total phospholipid of the pharmaceutical composition was about 5 umol.

Group 2: 5 rabbits each received 50 ul of the pharmaceutical composition comprising pre-formed liposomes and 0.2 mg of dexamethasone sodium phosphate (DSP), wherein total phospholipid of the pharmaceutical composition was about 5 umol.

Group 3: 5 rabbits each received 50 ul of the pharmaceutical composition comprising pre-formed liposomes and 0.6 mg of DSP, wherein total phospholipid of the pharmaceutical composition was about 5 umol.

Group 4: 5 rabbits were initially assigned to this group but 1 rabbit died under anesthesia prior to the intravitreal injection. Hence, 4 rabbits each received 50 ul of the pharmaceutical composition comprising pro-formed liposomes and 0.6 mg of DSP, wherein total phospholipid of the pharmaceutical composition was about 2.5 umol.

Group 5: 5 rabbits were initially assigned to this group but 1 rabbit died under anesthesia prior to the intravitreal injection. Hence, 4 rabbits each received 50 ul of the pharmaceutical composition comprising pre-formed liposomes and 0.6 mg of DSP, wherein total phospholipid of the pharmaceutical composition was about 1.25 umol.

The pharmaceutical composition was administered to the rabbit by intravitreal injection. The dose of DSP and the total amount of phospholipid administered to each eye, the number of eyes injected, the DSP strength and the phospholipid concentration of the pharmaceutical composition, and the volume of the pharmaceutical composition administered to each eye are summarized in Table 2.

TABLE 2

The characteristics of the pharmaceutical compositions

| Group Number | Dose of DSP per eye | Dose of PL* per eye | No. of eyes (No. of rabbits) | DSP strength (mg/mL) | PL* conc. (mg/mL) | Dose volume (ul/eye) |
|---|---|---|---|---|---|---|
| Group 1 | 0.05 mg | 5 umol | 10 (5) | 1 | 69.0 | 50 |
| Group 2 | 0.2 mg | 5 umol | 10 (5) | 4 | 69.0 | 50 |
| Group 3 | 0.6 mg | 5 umol | 10 (5) | 12 | 69.0 | 50 |
| Group 4 | 0.6 mg | 2.5 umol | 8 (4) | 12 | 34.5 | 50 |
| Group 5 | 0.6 mg | 1.25 umol | 8 (4) | 12 | 34.5 | 50 |

*PL = phospholipid

During the 180-day trial period, the rabbits were examined on regular intervals for the following outcomes:

Ocular adverse signs such as moderate cornea edema, corneal opacity, softened cornea (defined as the loss of corneal resilience using the tonometer on the cornea), and conjunctiva hyperemia. The eyes of the rabbits were examined on the following days: 0, 4, 7, 11, 14, 21, 25, 28, 32, 35, 39, 42, 46, 49, 53, 56, 60, 63, 67, 70, 74, 77, 82, 85, 89, 92, 96, 99, 103, 106, 110, 113, 117, 120, 124, 127, 131, 134, 138, 141, 145, 148, 152, 155, 159, 162, 166, 169, 173, 176 and 180.

Raised Intraocular pressure (IOP). The IOP was measured by Reichert Tono-Pen® XL Tonometer (Reichert, Inc. 3362 Walden Avenue, Depew, N.Y. 14034 USA) before intravitreal administration of the pharmaceutical composition and on the following days after the intravitreal administration: 0, 4, 7, 11, 14, 18, 21, 25, 28, 32, 35, 39, 42, 46, 49, 53, 56, 60, 63, 67, 70, 74, 77, 82, 85, 89, 92, 96, 99, 103, 106, 110, 113, 117, 120, 124, 127, 131, 134, 138, 141, 145, 148, 152, 155, 159, 162, 166, 169, 173, 176 and 180. Mice were determined to have raised IOP if the IOP was more than 15 mmHg.

Change in vitreous clarity. Liposomes were known to affect the vitreous clarity (B Short. Safety Evaluation of Ocular Drug Delivery Formulations: Techniques and Practical Considerations. *Toxicol Pathol*. January 2008; 36(1): 49-62 at 52). The vitreous clarity in the rabbits was assessed by direct ophthalmoscope (PanOptic Ophthalmoscope 118 series; Model 11820: Type 71000A; Welch Allyn Inc. 4341 State street road Skaneateles, N.Y. 13153-0220). The vitreous clarity was given a score of 0-4 (0 indicates a clear view of the retinal vessels; 1 indicates the retinal vessels are easily visualized through the pharmaceutical composition; 2 indicates a hazy view of the retinal vessels wherein vessels cannot be easily identified; 3 indicates a more hazy view wherein only a few retinal vessels can be identified; and 4 indicates vitreal haziness caused by the pharmaceutical composition).

In addition, the distribution of the pharmaceutical composition in the vitreous humor was evaluated using an ophthalmoscope. A fundus score was given between 0 (fundus visualized and was not covered by the pharmaceutical composition), 1 (one sixth of the fundus was covered by the pharmaceutical composition), 2 (one third of the fundus was covered by the pharmaceutical composition), 3 (one half of the fundus was covered by the pharmaceutical composition), 4 (two third of the fundus was covered by the pharmaceutical composition), 5 (five sixth of the fundus was covered by the pharmaceutical composition) to 6 (fundus was not visualized and fully covered by the pharmaceutical composition).

The results of the 180-day study are summarized in Table 3. These results show the rabbits receiving a pharmaceutical composition having less than about 2.5 umol of phospholipid (Group 4 and Group 5) displayed less ocular side effects relative to the rabbits receiving a pharmaceutical composition having at least about 5 umol of phospholipids (Group 3).

In addition, the pharmaceutical composition having less than about 2.5 umol of phospholipid (Group 4 and Group 5) are better distributed in the vitreous humor, due to a more rapid clearance in the vitreous humor relative to the pharmaceutical composition having at least about 5 umol of phospholipids (Group 3).

TABLE 3

The total incidence of ocular complications in Group 1 to Group 5 rabbits during the 180-day study

| Ocular Complication | Group 1 0.05 mg DSP & 5 umol PL* | Group 2 0.2 mg DSP & 5 umol PL* | Group 3 0.6 mg DSP & 5 umol PL* | Group 4 0.6 mg DPS & 2.5 umol PL* | Group 5 0.6 mg DPS & 1.25 umol PL* |
|---|---|---|---|---|---|
| Moderate Cornea Edema | 5/10 | 8/10 | 4/10 | Not detected | 4/8 |
| Corneal Opacity | 5/10 | 8/10 | 2/10 | Not detected | Not detected |
| Softened Cornea | 5/10 | 9/10 | 10/10 | 3/8 | 3/8 |
| Conjunctiva hyperemia | 6/10 | 6/10 | 3/10 | 1/8 | Not detected |
| Raised IOP | 6/10 | 8/10 | 4/10 | Not detected | 3/8 |
| Reduced Vitreal Clarity (score 3 or above | 2/10 | 2/10 | 1/10 | None | None |
| Fundus Score (Score 4 or above) | 4/10 | 2/10 | 2/10 | None | None |

*PL = Phospholipid

A more detail summary of the results in Table 3 is as follows:

Moderate Cornea Edema

The results show that the incidence of moderate cornea edema in Group 1, Group 2 and Group 3 rabbits (these rabbits received a pharmaceutical composition with more than 2.5 umol of phospholipid) are 50%, 80% and 40% respectively. There was no incidence of moderate cornea edema in Group 4 rabbits, and 50% of the Group 5 rabbits developed moderate cornea edema.

Corneal Opacity

50% of Group 1 rabbits, 80% of Group 2 rabbits and 20% of Group 3 rabbits developed corneal opacity, whereas none of the Group 4 and Group 5 rabbits had corneal opacity. In summary, rabbits receiving a pharmaceutical composition having less than about 25 umol of phospholipid (Group 4 and Group 5) displayed less corneal opacity relative to the rabbits receiving a pharmaceutical composition having at least about 5 umol of phospholipids Group 3).

Softened Cornea

The incidence of softened cornea was over 50% in Group 1, Group 2 and Group 3 rabbits, whereas the incidence of softened cornea was less than 50% in Group 4 and Group 5 rabbits. In summary, rabbits receiving a pharmaceutical composition having less than about 2.5 umol of phospholipid (Group 4 and Group 5) displayed less softened cornea relative to the rabbits receiving a pharmaceutical composition having at least about 5 umol of phospholipids (Group 3).

Conjunctive Hyperemia

60% of the rabbits in Group 1 and Group 2, and 30% of the rabbits in Group 3 developed conjunctiva hyperemia. Only 12.5% of the Group 4 rabbits and none of the Group 5 rabbit had conjunctiva hyperemia. In summary, rabbits receiving a pharmaceutical composition having less than about 2.5 umol of phospholipid (Group 4 and Group 5) displayed less conjunctiva hyperemia relative to the rabbits receiving a pharmaceutical composition having at least about 5 umol of phospholipids (Group 3).

Raised IOP

Raised IOP is a well known side effect of ocular steroid injection. The signs of raised IOP were detected in 60% of Group 1 rabbits, 80% of Group 2 rabbits and 40% of Group 3 rabbits, whereas raised IOP was not detected in Group 4 rabbits and was detected in 37.5% of Group 5 rabbits. In summary, rabbits receiving a pharmaceutical composition having less than about 2.5 umol of total phospholipid (Group 4 and Group 5) displayed less raised IOP relative to the rabbits receiving a pharmaceutical composition having at least about 5 umol of phospholipids (Group 3).

Reduced Vitreal Clarity

20% of the Group 1 and Group 2 rabbits and 10% of the Group 3 rabbits had reduced vitreal clarity (with a score 3 or more). No reduced vitreal clarity (with a score 3 or more) was found in Group 4 and Group 5 rabbits. In summary, the pharmaceutical composition having less than about 2.5 umol of total phospholipid (Group 4 and Group 5) is less likely to impair vitreous clarity relative to the pharmaceutical composition having at least about 5 umol of phospholipids (Group 3).

The Fundus Score

40% of the Group 1 and 20% of the Group 2 and Group 3 rabbits had a fundus score greater than 4, whereas none of the Group 4 and Group 5 rabbits had a fundus score greater than 4. In summary, the pharmaceutical composition having less than about 2.5 umol of phospholipid (Group 4 and Group 5) are better distributed in the rabbit's vitreous humor relative to the pharmaceutical composition having at least about 5 umol of phospholipids (Group 3).

What is claimed is:

1. A method of treating an ophthalmic disease and reducing the side effect of an ocular steroid, comprising administrating to a subject in need thereof an effective amount of a pharmaceutical composition, wherein the pharmaceutical composition comprising:
   (a) a lipid cake mixture comprising a phospholipid or a mixture of phospholipids; and
   (b) a steroid solution comprising an effective amount of an ocular steroid, or a pharmaceutically acceptable salt thereof;
      wherein the total amount of the phospholipids in the pharmaceutical composition ranges from about 0.1 $\mu$mol to about 2.5 $\mu$mol per 50 $\mu$l of the pharmaceutical composition, and wherein the ocular steroid side effect profile of the pharmaceutical composition is reduced, relative to the ocular steroid side effect of the pharmaceutical composition having at least about 5 $\mu$mol of phospholipids per 50 $\mu$l of the pharmaceutical composition.

2. The method of claim 1, wherein the ophthalmic disease is confined to the posterior segment of the eye.

3. The method of claim 1, wherein the ophthalmic disease is macular edema.

4. The method of claim 1, wherein the ophthalmic disease is uveitis.

5. The method of claim 1, wherein the ophthalmic disease is branch retinal vein occlusion.

6. The method of claim 1, wherein the ophthalmic disease is central retina vein occlusion.

7. The method of claim 1, wherein the ophthalmic disease is age-related macular degeneration.

8. The method of claim 1, wherein the pharmaceutical composition is administered by intravitreal injection.

9. The method of claim 1, wherein the lipid cake mixture further comprises cholesterol.

\* \* \* \* \*